US00PP16369P2

(12) United States Plant Patent
Bradford

(10) Patent No.: US PP16,369 P2
(45) Date of Patent: Mar. 21, 2006

(54) INTERSPECIFIC TREE NAMED 'PLUMSWEET V'

(50) Latin Name: ***Prunus* sp.**
Varietal Denomination: Plumsweet V

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 79 days.

(21) Appl. No.: 11/029,689

(22) Filed: Jan. 6, 2005

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP12,936 P2 * 9/2002 Zaiger et al. ..... Plt./180
PP13,476 P2 * 1/2003 Bradford ..... Plt./184
PP13,687 P2 * 3/2003 Zaiger et al. ..... Plt./180
PP14,247 P2 * 10/2003 Bradford ..... Plt./184

* cited by examiner

*Primary Examiner*—Anne Marie Grunberg
*Assistant Examiner*—W. C. Haas

(57) ABSTRACT

The present invention relates to an interspecific tree and more particularly to a new and distinct variety broadly characterized by medium size, vigorous, hardy, and self-unfruitful but productive tree. The present variety requires cross pollination from a plum that blooms during the mid season, such as 'Yummyrosa' (U.S. Plant Pat. No. 13,476). The fruit matures under the ecological conditions described during the latter part of August, with first picking on Aug. 20, 2003, and will hang on the tree for about twenty more days. The fruit is uniformly medium in size, blackish red over a deep reddish brown in skin color, clingstone in type, usually oblate in shape, grayish yellow with some red bleeding in flesh color, very firm and crisp in texture, and extremely sweet in flavor.

1 Drawing Sheet

CROSS-REFERENCE TO RELATED APPLICATIONS

The present application is related to co-pending U.S. Plant patent application Ser. No. 11/029,693.

Botanical classification: *Prunus* sp.

Varietal denomination: 'Plumsweet V'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumsweet V'.

During a typical blooming season I isolate as seed parents both individual and groups of different plum trees by covering them with screen houses. A hive of bees is placed inside each such house and bouquets to provide pollen from different plum, apricot, and interspecific plum-apricot hybrid trees are placed near the trees approximately every two days for the duration of the bloom. During 1997 one such house containing an unnamed red plum was crossed by me in this manner. To pollinate this red plum, I selected bouquets from several sources of apricot and interspecific plum-apricot hybrid trees without keeping specific written details. Upon reaching maturity the fruit from this red plum tree was harvested and the seeds were removed, cracked, stratified and germinated as a group with the label "38PH9". They were grown as seedlings on their own root in my greenhouse and, upon reaching dormancy, transplanted to a cultivated area of my experimental orchard at Bradford Farms near Le Grand, Calif. in Merced County (San Joaquin Valley). During the summer of 2001 the present variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is quite similar to 'August YUMMY' (U.S. Plant Pat. No. 14,247) plum by being self-unfruitful and by producing fruit that is dark red to purple in skin color, usually oblate in shape, firm in texture, mostly yellow with red bleeding toward the skin in flesh color, and clingstone in type, but is distinguished therefrom by producing fruit that is sweeter in flavor, somewhat smaller in size, and that matures about 10 days later.

SUMMARY OF VARIETY

The present interspecific fruit variety is characterized by a medium size, vigorous, hardy, and self-unfruitful but productive tree. Being self-unfruitful, the present variety requires cross pollination from a plum that blooms during the mid season, such as 'YUMMYrosa' (U.S. Plant Pat. No. 13,476). The present variety's abundance of blossoms and pollen entices strong bee activity to facilitate pollination. The fruit matures under the ecological conditions described during the latter part of August, with first picking on Aug. 20, 2003, and will hang on the tree for about twenty more days. The fruit is uniformly medium in size, blackish red over a deep reddish brown in skin color, clingstone in type, usually oblate in shape, grayish yellow with some red bleeding in flesh color, very firm and crisp in texture, and extremely sweet in flavor.

DRAWING

The accompanying photograph consists of four whole fruits positioned to display the characteristics of the skin color and form, two halves of one fruit divided transversely to the suture plane to reveal the flesh and stone, typical leaves and an inset depicting buds and flowers as they appear on the tree.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Sep. 5, 2003, on the original tree during its sixth growing season. The flower and bud descriptions were developed the following blooming season. All major color code designations are by reference to the Inter-Society Color Council, National Bureau of Standards. Common color names are also used occasionally.

TREE

Size: Medium, reaching and maintaining a height of 10' [3.1 m.] and a spread of 10' [3.1 m.] after six growing seasons utilizing typical dormant pruning.

Vigor: Vigorous, responding typically to irrigation and fertilization. The variety grows about 5' [1.5 m.] of surplus top-growth during the spring and summer. The plant should be grown on a standard commercial rootstock for production purposes.

Growth: Spreading and moderately open.

Form: Trained to be vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Productive, thinning usually necessary.

Fertility: Self-unfruitful, requiring cross pollination by a suitable mid seasonal blooming plum, such as 'YUMMY-rosa' (U.S. Plant Pat. No. 13,476).

Bearing: Usually consistent, but uncertain bearing can exist if inclement weather is encountered during the blooming period.

Trunk:

*Size.*—Medium, reaching a maximum diameter of 4⅛" [105 mm.] after the sixth growing season.

*Texture.*—Shaggy.

*Bark color.*—Dark grayish brown [62. d.gy.Br] variegated with Light brown [57. l.Br] crevices.

*Lenticels.*—Approximate Number Per Square Inch: 15. Color: Light orange [52. l.O]. Typical Size: ⅜" [9.5 mm.]. Shape: Eye-shaped to elongated.

Branches:

*Size.*—Diameter of main scaffold is 2¼" [57.2 mm.] measured 12" above the crotch, diameter of limb is 1 7/16" [36.5 mm.] measured 12" above the first fork, and dependent upon cultural practices and climatic conditions.

*Texture.*—Smooth on first year wood, increasing roughness with age.

*Color.*—1st Year Wood Topside: Moderate yellowish brown [77. m.yBr]. 1st Year Wood Underside: Brilliant yellow green [116. brill.YG]. Older Wood: Strong brown [55. s.Br] on second year wood, Dark Grayish brown [62. d.gy.Br] with Light yellowish brown [76. l.yBr] crevices on third year and older wood.

*Lenticels.*—Number Per Square Inch: More than 60 on second year wood. Color: Deep orange yellow [69. deep OY]. Typical size: 1/32" [0.8 mm] to ⅛" [3.2 mm.]. Shape: Eye-shaped to elongated.

Leaves:

*Size.*—Medium. Average Length: 4⅜" [111 mm.]. Average width: 2⅛" [54 mm.].

*Arrangement.*—Alternate.

*Thickness.*—Medium.

*Form.*—Elliptical.

*Apex.*—Acuminate.

*Base.*—Acute, with an average base angle of 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ⅝" [15.9 mm]. Average Thickness: 1/16" [1.6 mm.]. Color: Underside is Light yellow green [119. l.YG] and topside is Moderate red [15. m.R].

*Stipules.*—Number: 2 per leaf, up to 6 per growing tip. Average Length: 5/16" [7.9 mm.]. Color: Light yellow green [119. l.YG] with Dark pink [6. d.Pk] edges.

*Glands.*—Number: 0 to 4 per leaf. Position: No more than 2 on petiole, rest on base of blade. Size: Small. Form: Globose. Color: Brilliant yellow green [116. brill.YG] when young and Moderate reddish brown [43. m.rBr] with age.

*Leaf buds.*—Small, pointed and conic.

Flower buds:

*Hardiness.*—Hardy, with respect to central California winters.

*Diameter.*—Typically 3/16" [4.8 mm.] 3 days before bloom.

*Length.*—Typically ⅜" [9.5 mm.] 3 days before bloom.

*Form.*—Not appressed.

*Surface.*—Pubescent.

*Color.*—White [263. White].

Flowers: Perfect, complete, perigynous, usually a single pistil, typically thirty or more stamens, five sepals and petal locations alternately positioned.

*Average flower diameter.*—15/16" [23.8 mm.].

*Number of petals.*—Five, no double blossoms observed.

*Petal shape.*—Oval.

*Petal margin.*—Wavy.

*Average petal diameter.*—5/16" [7.9 mm.].

*Average petal length.*—⅜" [9.5 mm.].

*Petal apex.*—Rounded.

*Petal base.*—Rounded to somewhat cuneate.

*Petal color.*—White [263. White].

*Anther color.*—Brilliant orange yellow [67. brill.OY].
*Stigma color.*—Light greenish yellow [101. l.gY].
*Sepal color.*—Light yellow green [119. l.YG].
*Sepal length.*—5/32" [4.0 mm.].
*Sepal width.*—1/8" [3.2 mm.].
*Average pistil length.*—1/2" [12.7 mm.].
*Average stamen length.*—3/8" [9.5 mm.].
*Fragrance.*—Moderate.
*Pollen production.*—Abundant.
*Blooming period.*—Medium to slightly early compared with other varieties, about 5 days before 'Santa Rosa' (unpatented).
*Onset of bloom.*—One percent on Feb. 23, 2004.
*Date of full bloom.*—Mar. 4, 2004.
*Duration of bloom.*—One to two weeks, dependent on ambient temperature.
*Number per cluster.*—3 to 9, average 5.

FRUIT

Maturity when described: Hard eating ripe, Sep. 5, 2004.
Date of first picking: Aug. 20, 2003.
Date of last picking: Sep. 10, 2003.
Size: Medium, uniform.
*Average diameter axially.*—2 1/4" [57.2 mm.].
*Average diameter across suture plane.*—2 3/8" [60.3 mm.].
*Typical weight.*—4.8 ounces [136 grams].
Form: Somewhat oblate with some purely globose, symmetrical.
*Longitudinal section form.*—Circular to elliptical.
*Transverse section through diameter.*—Circular.
Suture: A very shallow groove extending from the stem cavity and discontinuing at the apex.
Ventral surface: Rounded, very slightly lipped.
Lips: Slightly unequal.
Cavity: Flaring, circular.
*Depth.*—3/8" [9.5 mm.].
*Breadth.*—15/16" [23.8 mm.].
Base: Somewhat truncate.
Apex: Rounded.
Pistil point: An inconspicuous Moderate yellow [87. m.Y] dot located at the end of the suture, occasionally upon a very slight hump.
Stem: Medium.
*Average length.*—3/8" [9.5 mm.].
*Average width.*—1/16" [1.6 mm.].
Skin:
*Thickness.*—Medium.
*Surface.*—Medium.
*Tenacity.*—Tenacious to flesh.
*Astringency.*—Slightly astringent.
*Tendency to crack.*—Slight.
*Color.*—Blackish red [21. blackish R] smoothly blending into a Deep reddish brown [41. deep rBr] background with heavy Light yellowish brown [76. l.yBr] freckling toward the apex and with multiple Moderate orange [53. m.O] circular lines on the shoulders around the stem cavity.
*Bloom.*—Abundant.
Flesh:
*Color.*—Grayish yellow [90. gy.Y] toward the stone with Dark red [16. d.R] bleeding very close to the skin.
*Surface of pit cavity.*—Clingstone, covered with very short Brownish pink [33. br.Pk] fibers breaking when twisted from the stone.
*Amygdalin.*—Moderate.
*Juice.*—Abundant, rich.
*Texture.*—Firm and extremely crisp.
*Fibers.*—Abundant, fine.
*Ripens.*—Slightly earliest at the apex and along the shoulders.
*Flavor.*—Mildly acidic but extremely sweet, 21 to 26 brix.
*Aroma.*—Very slight.
*Eating quality.*—Very best.

STONE

Type: Clingstone.
Form: Oval to oblong.
Hilum: Narrow, oval.
Base: Acute with average angle of 70 degrees and a v-shaped notch at the hilum.
Apex: Acuminate.
Sides: Equal.
Surface: Rough.
External color of stone: Grayish yellowish brown [80. gy.yBr] toward the apex and Light yellowish brown [76. l.yBr] toward the base.
Pit wall color when cracked: Light grayish yellowish brown [79. l.gy.yBr].
Cavity surface color: Moderate yellowish brown [77. m.yBr].
Average pit wall thickness: 1/16" [1.6 mm.].
Average width: 5/8" [15.9 mm.].
Average length: 1" [25.4 mm.].
Average breadth: 3/8" [9.5 mm.].
Tendency to split: Slight.
Kernel:
*Form.*—Oval.
*Skin color.*—Dark orange yellow [72. d.OY].
*Pellicle color.*—Moderate yellowish brown [77. m.yBr].
*Vein color.*—Deep yellowish brown [75. deep yBr].
*Taste.*—Bitter.
*Viable.*—Yes.
*Average width.*—7/16" [11.1 mm.].
*Average length.*—9/16" [14.3 mm.].
*Amygdalin.*—Moderate.

USE

Market: Fresh market and long distance shipping.
Keeping quality: Marginal, as fruit texture, juice, flesh color, and flavor observed to remain in good condition for 30 days in standard cold room at 36° Fahrenheit [2° Celsius], however wrinkling in the shoulder area occurs within 14 days.
Shipping quality: Average.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'August YUMMY' (U.S. Plant Pat. No. 14,247) plum by being self-unfruitful and by producing fruit that is dark red to purple in skin color, usually oblate in shape, firm in texture, mostly yellow with red bleeding toward the skin in flesh color, and clingstone in type, but is distinguished therefrom by producing fruit that is much sweeter in flavor, somewhat smaller in size, and that matures about 10 days later.

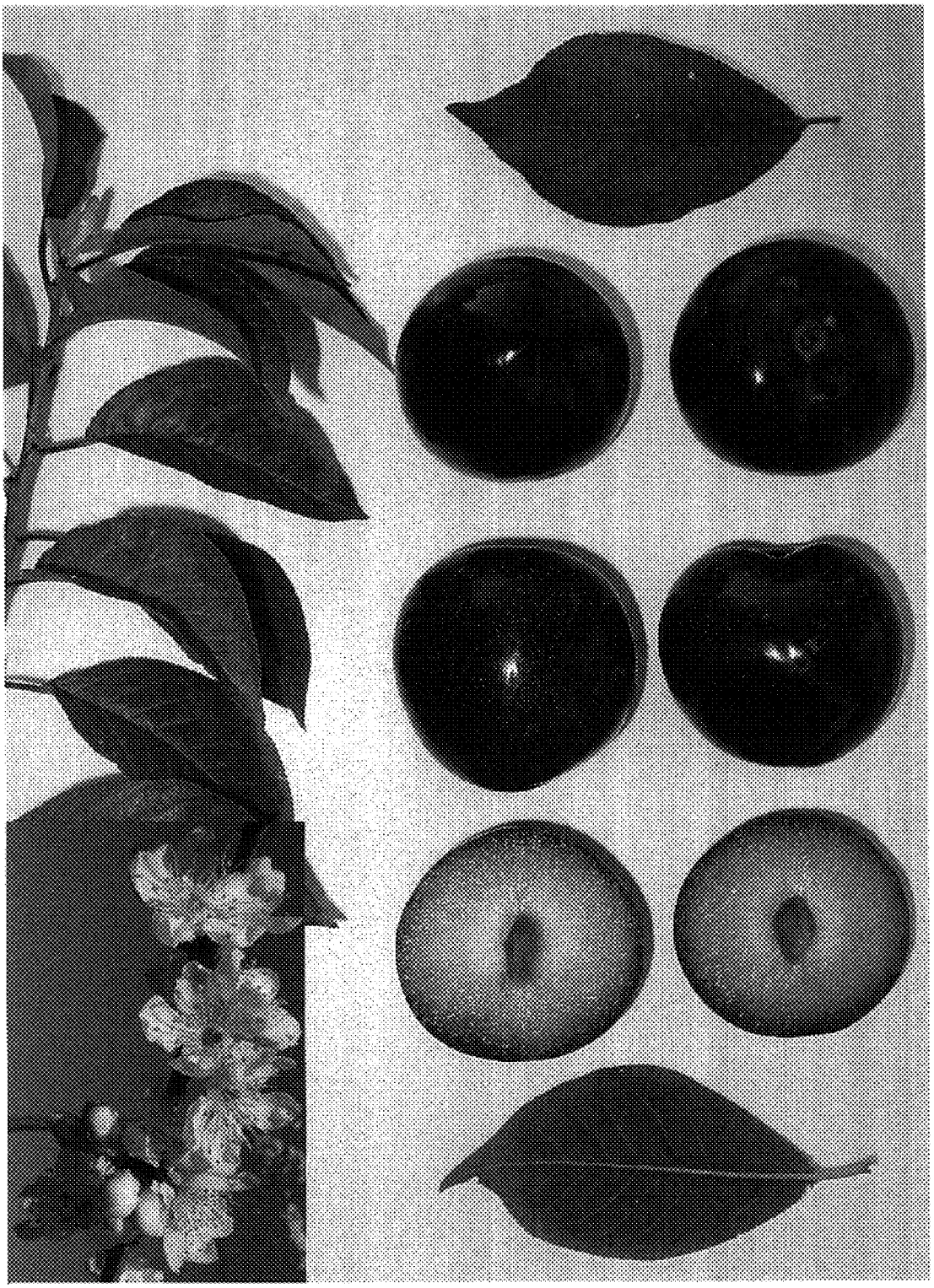

* * * * *